United States Patent

Jass

(10) Patent No.: US 6,323,359 B1
(45) Date of Patent: Nov. 27, 2001

(54) PROCESS FOR PREPARING PROBUCOL DERIVATIVES

(75) Inventor: Paul Alan Jass, Charles City, IA (US)

(73) Assignee: Salsbury Chemicals, Inc., Charles City, IA (US)

( * ) Notice: Subject to any disclaimer, the term of this patent is extended or adjusted under 35 U.S.C. 154(b) by 0 days.

(21) Appl. No.: 09/562,657

(22) Filed: May 2, 2000

(51) Int. Cl.$^7$ .................................................. C07C 9/00
(52) U.S. Cl. ............................................................ 560/142
(58) Field of Search ............................................. 560/142

(56) References Cited

FOREIGN PATENT DOCUMENTS

| 2140769 | * | 1/1973 | (FR) . |
| WO 9321914 | * | 11/1993 | (WO) . |
| WO 9851662 | * | 11/1998 | (WO) . |
| WO 9901118 | * | 1/1999 | (WO) . |

* cited by examiner

*Primary Examiner*—Paul J. Killos
(74) *Attorney, Agent, or Firm*—Richard J. Hammond

(57) ABSTRACT

A method is described for the preparation of water-soluble derivatives of probucol compounds having the following formula

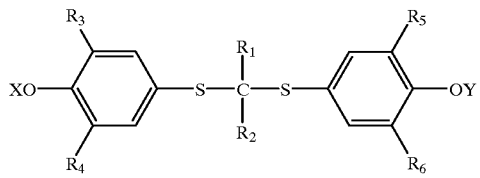

where $R_1$ and $R_2$ are the same or different and are alkyl, alkenyl or aryl having from 1 to 8 carbon atoms, $R_3$, $R_4$, $R_5$ and $R_6$ are the same or different and are alkyl having from 1 to 4 carbon atoms and X and Y are the same or different and are hydrogen or the groups saturated acyl or unsaturated acyl having from 1 to 8 carbon atoms said saturated or unsaturated acyl groups containing a polar or charged functionality.

The method for preparation of such compounds comprises reacting a solution of a probucol compound having the following formula where $R_3$, $R_4$, $R_5$ and $R_6$ are as previously defined with a compound selected from the group where $R_1$ and $R_2$ are methyl, $R_3$, $R_4$, $R_5$ and $R_6$ are tert-butyl and X is H or the group —C(O)—(CH$_2$)$_2$—C(O)OH and Y is the group —C(O)—(CH$_2$)$_2$—C(O)OH comprising reacting a solution of a probucol compound having the following formula where $R_3$, $R_4$, $R_5$ and $R_6$ are as previously defined with a compound selected from the group consisting of an alkali metal hydroxide, alkali metal alkoxide, alkyl ammonium alkoxide, alkyl ammonium hydroxide and mixtures thereof thereby forming an ammonium or an alkali metal salt of the probucol compound; reacting said salt with succinic acid anhydride and separating said water-soluble probucol compound.

9 Claims, No Drawings

PROCESS FOR PREPARING PROBUCOL DERIVATIVES

FIELD OF INVENTION

The present invention relates to a process for the preparation of derivatives of the antioxidant probucol. More particularly, the present invention relates to a process for preparing water-soluble derivatives of probucol compounds by reaction of the salts of such compounds with carboxylic acid anhydrides.

BACKGROUND OF THE INVENTION

Probucol is a well-known antioxidant that is chemically related to 2-[3]-tert-butyl4-hydroxyanisole, 2,6-di-tert-butyl4-methylphenol and the like. These materials are commonly used in foods to prevent oxidative deterioration. The compound probucol, 4,4'-(isopropylidenedithio) bis(2,6-di-tert-butylphenol), is represented by the following structural formula

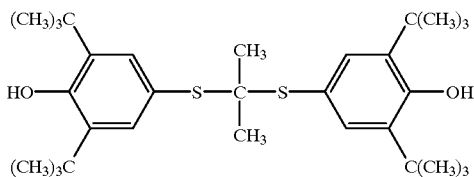

The preparation of this compound is a multistep process, starting by reacting a solution of the appropriately-substituted 4-mercaptophenol with acetone, in the presence of a catalytic amount of hydrochloric acid. Probucol precipitates from the reaction mixture and is readily separated and purified. The reaction is described in detail in U.S. Pat. No. 3,862,332 (Barhhart et al).

Similarly, probucol and certain of its derivatives is also described in U.S. Pat. No. 3,485,843 (Wang), U.S. Pat. No. 3,576,833 (Neuworth) and U.S. Pat. No. 4,985,465 (Handler).

As noted above, probucol is related to antioxidants found useful as food additives. However, this compound has also proven effective as a serum cholesterol-lowering agent for treating patients suffering from hypercholesterolemia. Further, probucol has been suggested as an effective antiviral compound (see U.S. Pat. No. 4,985,465 cited above) as well as a compound that may be active in treating arrhythmia (see U.S. Pat. No. 4,719,273 to McCaughn).

Administration of probucol itself into the human body is difficult because of its lack of solubility in aqueous solutions. While it cannot be injected intravenously and is poorly miscible in buffered solutions, solid dosage forms such as tablets or capsules are commercially available for administration. Unfortunately, even this route is subject to problems, since uptake by the body is poor. It appears that patients administered the same concentration of probucol obtain sera levels of the compound that differ by as much as 20 times. In order to avoid the low water solubility problems associated with probucol utilization in the body, water-soluble derivatives have been prepared that spontaneously hydrolyze in aqueous environments to probucol. Thus, U.S. Pat. No. 5,262,439 (Parthasarathy), incorporated herein in its entirety by reference, disclose a class of water-soluble probucol derivatives having one or more ester groups replacing the phenolic hydroxyl group of the probucol molecule. Some of the compounds disclosed in this reference have polar or charged functionalities attached to the ester group, e.g., the groups carboxylic acid, amide, amino, and aldehyde. The method for preparing these water-soluble probucol compounds involves the treatment of a solution of probucol with the carboxylic acid anhydride compound bearing the desired polar or charged functionality in the presence of a catalyst. The catalyst is disclosed to be 4-(dimethylamino)pyridine. While the reaction is relatively simple in concept, the isolation of the desired derivative is complex to the point that economically acceptable yields of these water-soluble derivatives is not possible.

Accordingly, there is a need for a method to prepare water-soluble derivatives of probucol that is simple and provides the di sired compound in good yields.

SUMMARY OF THE INVENTION

A method is described for the preparation of water-soluble derivatives of probucol compounds having the following formula

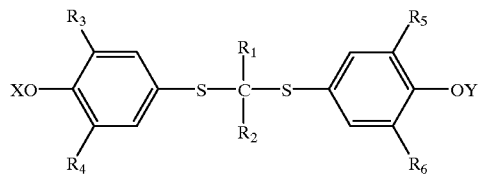

where $R_1$ and $R_2$ are the same or different and are alkyl, alkenyl or aryl having from 1 to 8 carbon atoms, $R_3$, $R_4$, $R_5$ and $R_6$ are the same or different and are alkyl having from 1 to 4 carbon atoms and X and Y are the same or different and are hydrogen or the groups saturated acyl or unsaturated acyl having from 1 to 8 carbon atoms said saturated or unsaturated acyl groups containing a polar or charged functionality. The method for preparation of such compounds

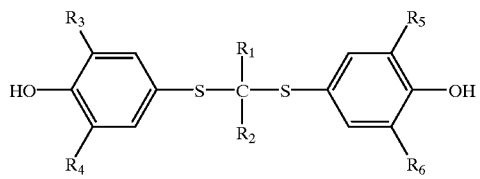

where $R_3$, $R_4$, $R_5$ and $R_6$ are as previously defined with a compound selected from the group consisting of alkali metal hydride, alkali metal hydroxide, alkali metal alkoxide, alkyl ammonium alkoxide, alkyl ammonium hydroxide and mixtures thereof. The reaction forms a solution of the ammonium or alkali metal salt of the probucol compound, which may be separated from the reaction mass and further reacted or, more conveniently, used "as is" in the subsequent, second, reaction step. In such second step, the salt (or the "as is" reaction solution) is reacted with a carboxylic acid anhydride selected from the group consisting of succinic acid anhydride, glutaric acid anhydride, adipic acid anhydride, suberic acid anhydride, sebacic acid anhydride, azelaic acid anhydride, phthalic acid anhydride and maleic acid anhydride. The water-soluble probucol compound is then separated from the resulting reaction mixture.

DESCRIPTION OF THE PREFERRED EMBODIMENTS

The present invention provides a process for preparing water-soluble probucol compounds that is an improvement over the prior art processes.

The process of the present invention utilizes a starting material that is a probucol compound having the following formula

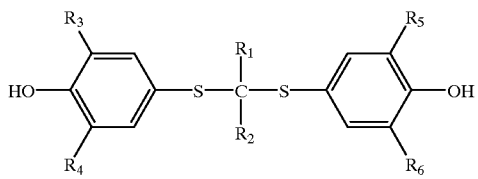

where $R_1$ and $R_2$ are the same or different and are alkyl, alkenyl or aryl having from 1 to 8 carbon atoms and $R_3$, $R_4$, $R_5$ and $R_6$ are the same or different and are alkyl having from 1 to 4 carbon atoms.

Preferably, $R_1$ and $R_2$ are the same and are alkyl having from 1 to 8 carbon atoms, most preferably methyl.

Preferably, $R_3$, $R_4$, $R_5$ and $R_6$ are the same and are alkyl having from 1 to 4 carbon atoms, most preferably tert-butyl.

As a first step in the method for preparing water-soluble probucol compounds according to the present invention, the hydroxyl groups of probucol compounds illustrated above are reacted with a compound that forms an alkali metal or ammonium salt of such probucol compounds. These materials are highly basic reactants and are selected from the group consisting of alkali metal hydride, alkali metal hydroxide, alkali metal alkoxide, alkyl ammonium alkoxide, alkyl ammonium hydroxide and mixtures thereof.

The alkyl group as disclosed herein, such including the alkyl group of alkoxides, is $C_1$ to $C_8$ alkyl and includes the moiety's methyl, ethyl, n-propyl, i-propyl, n-butyl, sec-butyl, tert-butyl, n-pentyl, 2-methylpentyl, n-octyl and the like.

Preferably the alkali metals of these reactants are lithium, sodium, potassium and cesium, most preferably sodium or potassium with potassium being especially preferred.

A particularly preferred reactant used to produce the salt of the probucol compounds are sodium or potassium butoxide.

The salt of the probucol compound prepared in the first step as set forth above is next reacted with a compound that contains a group reactive with the ammonium or alkali metal phenoxide formed at the 4- and 4'-positions of the bisphenol moiety. Such compounds may be described as those that are saturated or unsaturated acyl that have attached to them groups that bear a polar or charged functionality. Illustrative classes of compounds of this nature are saturated or unsaturated dicarboxylic acids, amines, amides, aldehydes or salts of such compounds.

In the most preferred embodiment, second step of the above class of reactants with the salt of probucol compounds formed in the first step of the process of the invention are dicarboxylic acids, dicarboxylic acid anhydrides and the salts thereof such compounds having from 2 to 8 carbon atoms, the salts including the alkali metal salts, alkaline earth metal salts, ammonium salts, the transition metal salts, the noble metal salts and the heavy metal salts of such dicarboxylic acids or acid anhydrides.

Particularly preferred reactants with the salt of the probucol compounds formed in the first step of the process of the present invention are the carboxylic acid anhydride reactants selected from the group consisting of succinic acid anhydride, glutaric acid anhydride, adipic acid anhydride, suberic acid anhydride, sebacic acid anhydride, azelaic acid anhydride, phthalic acid anhydride and maleic acid anhydride (these acid anhydrides are also referred to as "anhydride", e.g., succinic acid anhydride is also referred to as succinic anhydride). Especially preferred in the second step reaction of the salt of the probucol compound with the particularly preferred reactants is succinic acid anhydride. In such particularly preferred case, the water soluble derivatives resulting from the process of the present invention are those where X is H or "—C(O)—(CH$_2$)$_2$—C(O)OH" and Y is "—C(O)—(CH$_2$)$_2$—C(O)OH."

The first step of the reaction of the present invention is carried out by admixing a solution of the probucol compound with the inorganic salt at about room temperature for about from one to about four hours.

From this first step, the salt of the probucol compound readily forms. It may be separated as a solid from the reaction solution by, for example, removal of the solvent and subsequent filtration or by any other conventional means. The separated salt can then be used in the second step of the process of the present invention.

It may be desirable, however, to proceed to the second step of the process of the present invention without separating the salt from the reaction solution, i.e., the reaction solution from step one is used to initiate the second step "as is", i.e., without further processing.

In any case, in the second step of the process of the present invention a solution of the salt of the probucol compound produced in step one is reacted with a compound that contains a group reactive with the phenolic hydroxylic group on the 4- and 4'-position of the bisphenol moiety. These compounds have already been described. The reaction is typically carried out from about 1 to about 5 hours in a solution of an organic solvent and produces the desired water-soluble derivative of the probucol compound. This compound is easily separated from the reaction mixture by a variety of conventional means, e.g., decantation, filtration, etc. In most cases, a single recrystallization of the separated water-soluble probucol compound produces the pure compound.

The following examples are provided for the purposes of illustration only. They are not meant to limit the invention in any way.

EXAMPLES

Example 1

To an appropriately sized, nitrogen-purged, glass reaction vessel is charged 375 mL anhydrous (0.01% water) tetrahydrofuran (THF) at 20–25° C. To the stirred THF solution is added 23.44 g, 199 mmol, 2.14 equivalents of potassium butoxide (KOtBu). To the resulting hazy solution is added 48.5 g, 93 mmol, 1.0 equivalent of 99% pure probucol in three equal portions. The orange-yellow colored solution is stirred for 45 minutes. A temperature drop from about 35° to about 22° C. is noted. To this solution is added 32.9 g, 326 mmol, 3.5 equivalents of succinic anhydride (SSA) over a period of about 90 seconds. The solution color first becomes brown and then deep blue. A temperature of about 25° results. Analysis by HPLC of the reaction mixture at this point shows a ratio of 3:10:7 disuccinyl probucol (DSP): monosuccinyl probucol (MSP): probucol (PRO). After washing twice with 12–14% sodium hydroxide, the solution is concentrated to about 25% of its original volume under reduced pressure at 45° C. The resulting slurry is diluted with 110 mL heptanes, and concentrated under reduced pressure two times. The final slurry amounts to about 150 mL of material. It is diluted with 400 mL heptanes, cooled col; DMAP is 4-dimethylamino)pyridine; DABCO is 1,4-diazabicyclo[2.2.2.]octane; KOH is potassium hydroxide; ALIQUAT® 336 is tricaprylmethylammonium chloride; and TEA Cl is tetraethylammonium chloride.

TABLE

| Example | Base (mol. equivalent) | DSP | MSP | Probucol | Reaction Time (hrs) | Temp ° C. |
|---|---|---|---|---|---|---|
| 2 | KOtBu(2.21) | 15.10 | 48.66 | 36.19 | 2.0 | Ambient |
| 3 | DMAP(2.18) | 0 | 0.14 | 98.65 | 2.0 | 29 |
|   |   | 0 | 1.17 | 96.82 | 18.0 | 30 |
| 4 | KOtBu(2.10) | 13.20 | 46.48 | 40.33 | 2.0 | 30 |
| 5 | DABCO(2.21) | 0.59 | 12.23 | 87.18 | 3.0 | 60 |
| 6* | KOtBu(2.10) | 6.68 | 37.78 | 55.37 | 2.0 | 30 |
|   |   | 8.51 | 37.73 | 55.76 | 78.5 | 60 |
| 7 | KOtBu(1.00) | 4.11 | 29.97 | 66.32 | 2.0 | 30 |
| 8 | KOtBu(5.10) | 12.13 | 45.34 | 42.11 | 1.9 | 30 |
| 9 | KOH(2.20) | 0.30 | 10.60 | 88.80 | 2.0 | Ambient |
| 10 | KOtBu(2.20) ALIQUAT ®336 (2.20) | 22.60 | 25.50 | 72.00 | 2.0 | Ambient |
| 11 | KOH(2.2) TEA Cl(2.2) | 5.50 | 33.40 | 61.2 | 2.0 | Ambient |
| compatative | KOtBu(0.10) | 0 | 0 | 100.00 | 2.0 | 30 |

*acrylonitrile, 150 mL was used in place of THF
Note: In Examples 10 and 11, a reaction between the two components shown in the column "Base (mol. equivalent)" precipitates potassium chloride, generating the respective alkylammonium alkoxide or alkylammonium hydroxide in situ.

to 0–5° C. with stiring and vacuum filtered. The residue is washed with 250 mL heptanes and, to the wet cake is added 65 mL tert-butylmethyl ether (MBTE) with string. The resulting slurry is filtered, the residue washed with 23 mL MBTE and the filtrate washed with 40 mL 1.3 N hydrochloric acid containing 2.5 g sodium chloride. The solution is dried azeotropically at 40° C. with the addition of about 200 mL of MBTE. The resulting residue is diluted with 200 mL heptanes, warmed to 70° C. and seeded with 15 mg MSP. After cooling the seeded solution to 5° C. over a period of about 18 hours, the cold slurry is filtered, washed with 100 mL heptanes and dried to yield off-white solid MSP, 23.2 g, 40.1 mmol %, 98.7 AP. The filtrate, containing free probucol is treated as shown below.

Probucol Recovery: The heptanes filtrate obtained in the above process is concentrated to about 350 mL, washed with 40 mL 1 N HCl and further concentrated to about 80 mL at 75° C. under reduced pressure. The solution is seeded and cooled to about 0 –5° C. and held at this temperature overnight. Filtration, washing the residue with heptanes and drying produces white, crystalline probucol, 10.33 g, 21.3 mol %, 99.91 AP. The mother liquor provides an additional 6.1 g, 12.6 mol %, 99.91 AP of probucol.

Example's 2–11

The above procedure of Example 1 is used to produce the water soluble derivatives of probucol exemplified below in the TABLE, Examples 2–11. In these Examples, the reaction employs 1 mol. equivalent of probucol, 150 mL (7.5:1, vol./wt starting PRO) TBF solvent (unless otherwise noted) and 3.51 equivalents of succinic anhydride. The reaction sequence and all other conditions are the same as used in Example 1.

In the TABLE: KOtBu is potassium butoxide; MSP is monosuccinylated probucol; DSP is disuccinylated probu-

I claim:
1. A process for the preparation of a water-soluble derivative of a probucol compound having the following formula

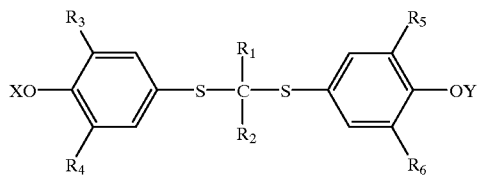

where $R_1$ and $R_2$ are the same or different and are alkyl, alkenyl or aryl having from 1 to 8 carbon atoms, $R_3$, $R_4$, $R_5$ and $R_6$ are the same or different and are alkyl having from 1 to 4 carbon atoms and X and Y are the same or different and are hydrogen or the groups that are saturated acyl or unsaturated acyl having from 1 to 8 carbon atoms said saturated acyl or unsaturated acyl groups containing a polar or charged functionality comprising reacting a solution of a probucol compound having the following formula

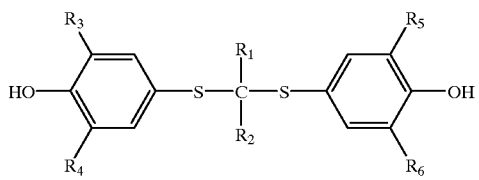

where $R_3$, $R_4$, $R_5$ and $R_6$ are as previously defined with a compound selected from the group consisting of alkali metal hydroxide, alkali metal alkoxide, alkyl ammonium alkoxide, alkyl ammonium hydroxide and mixtures thereof thereby forming an ammonium or an alkali metal salt of the probucol compound; reacting said salt with a carboxylic acid anhydride selected from the group consisting of succinic acid anhydride, glutaric acid anhydride, adipic acid anhydride, suberic acid anhydride, sebacic acid anhydride, azelaic acid anhydride, phthalic acid anhydride and maleic acid anhydride and separating said water-soluble probucol compound.

2. The process according to claim 1 wherein $R_1$ and $R_2$ are the same and are alkyl having from 1 to 8 carbon atoms.

3. The process according to claim 2 wherein $R_3$, $R_4$, $R_5$ and $R_6$ are the same and are alkyl having from 1 to 4 carbon atoms.

4. The process according to claim 1 wherein $R_1$ and $R_2$ are the same and are methyl.

5. The process according to claim 4 wherein $R_3$, $R_4$, $R_5$ and $R_6$ are the same and are tert-butyl.

6. The process according to claim 1 wherein the alkali metal is lithium, sodium, potassium or cesium.

7. The process according to claim 1 wherein the reactant is sodium tert-butoxide or potassium tert-butoxide.

8. The process according to claim 1 wherein said alkali metal salt of the probucol compound is reacted with succinic acid anhydride.

9. A process for the preparation of a water-soluble derivative of a probucol compound having the following formula

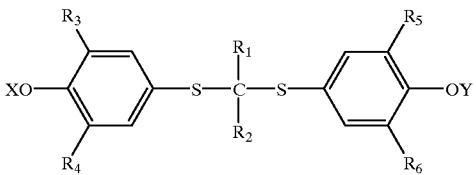

where $R_1$ and $R_2$ are methyl, $R_3$, $R_4$, $R_5$ and $R_6$ are tert-butyl and X is H or the group —C(O)—(CH$_2$)$_2$—C(O)OH and Y is the group —C(O)—(CH$_2$)$_2$—C(O)OH comprising reacting a solution of a probucol compound having the formula

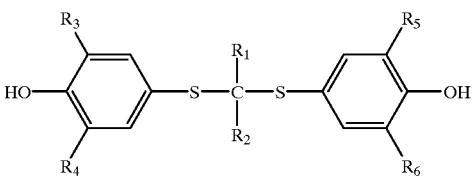

where $R_1$, $R_2$, $R_3$, $R_4$, $R_5$ and $R_6$ are as previously defined with a compound selected from the group consisting of alkali metal hydroxide, alkali metal alkoxide, alkyl ammonium alkoxide, alkyl ammonium hydroxide and mixtures thereof thereby forming a salt of said probucol compound, reacting said salt with succinic anhydride and separating said water-soluble probucol compound.

* * * * *